US010905413B2

(12) United States Patent
Valnicek

(10) Patent No.: US 10,905,413 B2
(45) Date of Patent: Feb. 2, 2021

(54) SURGICAL SUTURE ADAPTED FOR ENHANCED VISIBILITY

(71) Applicant: Stanley Michael Karl Valnicek, Kelowna (CA)

(72) Inventor: Stanley Michael Karl Valnicek, Kelowna (CA)

(73) Assignee: Dr. Stan M. Valnicek Inc., Kelowna (CA)

(*) Notice: Subject to any disclaimer, the term of this patent is extended or adjusted under 35 U.S.C. 154(b) by 668 days.

(21) Appl. No.: 15/337,758

(22) Filed: Oct. 28, 2016

(65) Prior Publication Data

US 2017/0119383 A1 May 4, 2017

Related U.S. Application Data

(60) Provisional application No. 62/247,332, filed on Oct. 28, 2015.

(51) Int. Cl.
*A61B 17/06* (2006.01)
*A61B 90/00* (2016.01)

(52) U.S. Cl.
CPC .. *A61B 17/06166* (2013.01); *A61B 17/06066* (2013.01); *A61B 90/39* (2016.02);
(Continued)

(58) Field of Classification Search
CPC .............. A61B 90/39; A61B 17/06066; A61B 17/06166; A61B 2090/3941; A61B 2017/0608
See application file for complete search history.

(56) References Cited

U.S. PATENT DOCUMENTS

| 2,143,077 A | 1/1939 | Leverenz et al. |
| 2,267,999 A | 12/1941 | Switzer |

(Continued)

FOREIGN PATENT DOCUMENTS

| CN | 202015212 | 10/2011 |
| CN | 203988180 | 12/2014 |

(Continued)

OTHER PUBLICATIONS

Rashmin S. Thakor et al., Project Report titled Sutures and Ligatures, dated 2004-2005, by North Gujarat University, Patan.
(Continued)

*Primary Examiner* — Phong Son H Dang
(74) *Attorney, Agent, or Firm* — Antony C. Edwards

(57) ABSTRACT

A surgical suture having enhanced visual characteristics is provided. The suture has a suture filament operatively coupled to a suture needle. The suture filament includes a useful segment and a terminal segment. The terminal segment is located at a first end of the filament. The useful segment extends substantially from the terminal segment to a second end of the filament. The terminal segment is of a length of the filament that is left-over after a substantially last formable suture knot is formed using the useful segment. After the last formable suture knot is formed, the terminal segment is removed from the useful segment along with the suture needle for disposal. In order to enable visual location of the terminal segment after the same has been separated from the useful segment, the filament is treated such that that the terminal segment has distinctive contrasting light frequency characteristics.

11 Claims, 1 Drawing Sheet

(52) U.S. Cl.
CPC ............... *A61B 2017/0608* (2013.01); *A61B 2090/3941* (2016.02)

(56) References Cited

U.S. PATENT DOCUMENTS

| | | | |
|---|---|---|---|
| 2,864,771 A | 12/1958 | Switzer et al. | |
| 3,949,755 A * | 4/1976 | Vauquois | D06P 1/0004 606/229 |
| 4,895,740 A | 1/1990 | Hiromori | |
| 4,905,695 A | 3/1990 | Bendel | |
| 5,286,922 A * | 2/1994 | Curtiss | H01B 5/008 174/112 |
| 6,053,870 A | 4/2000 | Fulton, III | |
| 6,610,071 B1 * | 8/2003 | Cohn | A61B 17/06166 606/148 |
| 7,147,615 B2 * | 12/2006 | Wariar | A61M 5/158 604/6.16 |
| 2002/0029032 A1 * | 3/2002 | Arkin | A61B 17/00 606/1 |
| 2005/0096698 A1 | 5/2005 | Lederman | |
| 2005/0222617 A1 * | 10/2005 | Ororz, Jr. | A61B 90/92 606/223 |
| 2007/0005071 A1 | 1/2007 | Kucklick | |
| 2008/0051833 A1 * | 2/2008 | Gramuglia | A61B 17/06128 606/222 |
| 2009/0318962 A1 * | 12/2009 | Spedden | A61L 17/005 606/228 |
| 2010/0274282 A1 * | 10/2010 | Olson | A61B 17/06166 606/228 |
| 2011/0264138 A1 * | 10/2011 | Avelar | A61B 90/94 606/228 |
| 2011/0319932 A1 * | 12/2011 | Avelar | A61B 17/06166 606/228 |
| 2013/0267942 A1 | 10/2013 | Fulton, III | |
| 2014/0171793 A1 * | 6/2014 | Lin | A61B 8/0841 600/424 |
| 2017/0119383 A1 * | 5/2017 | Valnicek | A61B 17/06066 |
| 2018/0185025 A1 * | 7/2018 | Gorek | A45F 5/00 |

FOREIGN PATENT DOCUMENTS

| | | |
|---|---|---|
| WO | 9402071 | 2/1994 |
| WO | 0147438 | 7/2001 |
| WO | 2004/096305 | 11/2004 |
| WO | 2007005621 | 1/2007 |
| WO | 2009/151876 | 12/2009 |

OTHER PUBLICATIONS

Article entitled "GLO-STITCH Monofilament Fluorescent Green Polypropylene Non-Absorbable Suture", sourced from www.cpmedical.com.

* cited by examiner

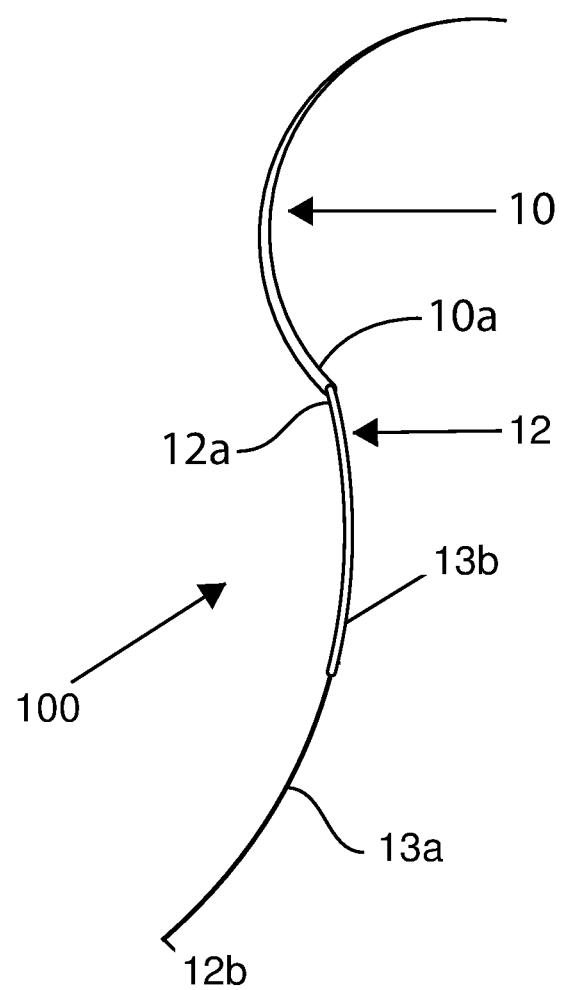

SURGICAL SUTURE ADAPTED FOR ENHANCED VISIBILITY

CROSS REFERENCE TO RELATED APPLICATIONS

This application claims priority from U.S. Provisional Application No. 62/247,332, filed on Oct. 28, 2015, entitled: "Surgical Suture Adapted for Enhanced Visibility", the entirety of which is incorporated herein by reference.

FIELD OF THE INVENTION

The present invention relates to a surgical suture with enhanced visual characteristics to increase its visibility in cluttered or low contrast environments.

BACKGROUND OF THE INVENTION

It is not uncommon in the operating room for surgical sutures to be lost. As used herein, reference to a surgical suture, or "suture", includes a needle and an attached fixed length of filament. The needle is used by a surgeon to penetrate a patient's tissue and the filament is used to draw tissue together and fasten it by means of a knot. The problem arises for example when the surgeon has made a sufficient number of stitches using a particular suture so as to have used up the useful length of the suture filament, leaving only the needle and a short length of remaining filament which is too short to be useful. Once the suture is thus ready to be discarded, as conventionally such sutures are one-time-use, the surgeon will place the suture where it may be retrieved and disposed of by a nurse, thereby freeing up the surgeon to continue with a fresh suture. When the sutures are inadvertently lost during surgery, it is possible that the suture has been left within the patient, but more commonly the lost suture has fallen on to the sterile field, drapes, clothing or floor. It is often difficult in these latter circumstances to locate the suture. Of course it is a matter of potentially grave concern if a suture cannot be found, as it may lie within the patient.

Despite preventative protocols, the problem of lost surgical articles remains an issue. A survey published by the Risk Management Foundation for the Harvard Medical Institutions (for all malpractice claims filed against Harvard-affiliated institutions) revealed that the third most common allegation was "retained foreign body".

In applicant's experience, surgeons and surgical nurses commonly adopt the procedure of counting, after each surgery, the entire contents of needles, sutures and other instruments in the supply table. Therefore, lost items must be located, so that the same numbers of items counted in are counted out. Retrieving lost sutures requires time and involves visual searching and may include various types of magnetic or fabric mops to run across the floor in an effort to pick up the lost suture.

It is known in the prior art to color a needle or suture along the entire length of the filament.

For example, in the prior art applicant is aware of a product marketed under the name Glo-Stitch™. It is described as a monofilament polypropylene non-absorbable, sterile surgical suture, composed of a strand of polypropylene which has been dyed fluorescent green along the entire length of the strand.

Published Patent Cooperation Treaty patent application WO1994/002071, entitled "Fluorescent Synthetic Sutures" also discloses a surgical suture of improved visibility comprising a sterile, synthetic filament having incorporated therein an effective amount of a coloured fluorescent dye. The synthetic filament is described as exhibiting a distinctive colour under visible light and that it is adapted to fluoresce a bright colour during exposure to ultraviolet (UV) radiation. It is taught to soak the entire suture in bright coloured fluorescent dye. The suture is taught for use in animals primarily.

U.S. Pat. No. 3,949,755 to Vauguois entitled "Surgical Ligature" describes a surgical ligature comprising a braid of filaments on which there is a succession of areas of contrasting shades, wherein at least one of the shades appears dark through a film of blood and at least one of the shades appears light through a film of blood or against an organ being stitched. It is taught that the individual filaments can be dyed in a full bath and the filaments extruded from synthetic materials, for example, polyester or polyamide, or regenerated materials, for example, collagen.

Conventional sutures are commercially available in standardized sizes, typically expressed in terms of the diameter of the suture or in terms of a corresponding coded size regime. Thus for example for micro-surgery a size 10/0 suture having a corresponding diameter of 0.05 mm may be employed, and for non-micro-surgery for example a size 0 suture having a corresponding diameter of 0.4 mm may be employed. However, the standardized size coding or suture diameter does not inform of the length of the suture filament other than generally a micro-surgery suture will have a shorter filament than a non-micro-surgery filament. Thus for example in applicant's experience a size 10/0 suture may have a filament which is approximately five inches long, and size 0 or 2 sutures may have filaments which are typically 24-36 inches long. A standardized suture size chart is provided as illustrative Table 1.

SUMMARY OF THE INVENTION

In a first embodiment of an apparatus according to the present invention, the suture filament may be described as having first and second opposite ends and a length therebetween. The first end of the filament is mounted or mountable into a secured and operative engagement with the base end of a suture needle. The base end is opposite from the sharp, distal or free end of the needle. The length of the filament may usefully be described as having a useful segment and a terminal segment. The terminal segment is located at the first end of the filament; that is, adjacent the base end of the needle. The terminal segment extends along the filament by a short distance; for example, not exceeding six inches or so. The useful segment of the filament extends substantially from the terminal segment to the opposite second or free end of the filament. The terminal segment may be described as the length of the suture filament that is leftover after a last suture knot is formed or tied so as to use-up the useful length of the filament within the patient. The terminal segment and needle are then removed, conventionally by cutting the filament so as to sever the terminal segment from the useful segment. The terminal segment and suture needle are then disposed of. Only the terminal segment of the filament is adapted for enhanced visibility so as to be fluorescently responsive with a bright colour upon exposure to ultraviolet light or otherwise treated to be highly contrastingly visible.

According to a further aspect of the invention, the apparatus is used in a corresponding method. The method comprises forming at least one surgical knot in a body using the useful segment of the suture filament and the surgical needle operatively coupled to the suture filament. The method further comprises severing from the useful segment the terminal segment along with the surgical needle after the useful segment has been expended. The method finally comprises visually detecting the terminal segment and the suture needle based on the distinctive contrasting light frequency characteristics of the terminal segment.

In detail, the suture filament comprises a first end mounted to a base end of the suture needle. Again, the suture filament presents a useful segment and an adjacent terminal segment between the useful segment and base end of the needle. During a surgical procedure, after a substantially last formable suture knot or stitch is formed using the useful segment, the terminal segment and the suture needle are then removed by severing the terminal segment from the useful segment. The needle and terminal segment of the suture filament are then disposed of and are easily detected based on the distinctive contrasting light frequency characteristics of the terminal segment.

In another embodiment, a method of manufacturing a suture filament having enhanced visual characteristics is provided. The method comprises extruding at least one bioabsorbable or nonbioabsorbable polymer to provide a suture filament of a predetermined length. The suture filament defines a useful segment and a terminal segment. The terminal segment is disposed at about a first end of the suture filament and the useful segment extends substantially from the terminal segment to a second end of the suture filament. The method further comprises treating the terminal segment such that it has distinctive contrasting light frequency characteristics. The distinctive contrasting light frequency characteristics enable easy visual location of the terminal segment after use of the suture filament.

BRIEF DESCRIPTION OF THE DRAWINGS

Table 1 lists a range of gauge sizes of sutures and corresponding diameters.

FIG. 1, in partially cut-away plan view, is one embodiment of a surgical suture described herein prior to its use as also described herein.

DEFINITIONS

Unless defined otherwise, all technical and scientific terms used herein have the same meaning as commonly understood by one of ordinary skill in the art to which this invention belongs.

As used herein, the terms:

"Fluorescent" refers any material that imparts colour under visible light and which emits highly visible colour in pre-determined wavelength ranges when excited by ultra-violet radiation (UV).

"Suture" refers to a surgical needle and its attached filament used to stitch together tissues, for example tissues of a living body.

"Specular" refers to its common meaning, e.g., of, relating to, or having the qualities of a mirror, and may be any reflective surface which reflects a light source.

"Light sources" may include light emitting diodes (LEDs), coherent light sources or lasers, ultra-violet UV light sources, or other light emitters.

"Brightly coloured" means any vivid colour so as to enhance visibility by providing an eye-catching contrast, in this case so as to visually more easily see, by reason of the contrast, a needle or suture against a background colour of the floor, upon the drapes around the sterile field, within the patient or upon the clothing of the surgeon and attending nurses, and any of these which may also include the colour of blood that may be on them "Terminal Segment" means the length of the suture filament that is leftover after a last suture knot is formed or tied so as to use-up the useful length of the filament.

"Useful Segment" means the free end of the suture filament adjacent the terminal segment.

DETAILED DESCRIPTION OF EMBODIMENTS OF THE INVENTION

In order to solve the problems described above, the present invention provides a surgical suture including a surgical suture filament having enhanced visual characteristics to enhance the visibility of a terminal end or segment of the filament.

FIG. 1 is a representation of one embodiment of a surgical suture 100 prior to its use in sewing together body tissues (not shown). The suture 100 includes a filament 12 which is in operative engagement with a suture needle 10. The suture filament 12 has first and second opposed ends, 12a and 12b, respectively and a length extending between the opposed ends 12a and 12b. In one embodiment, first end 12a of the filament 12 is secured to a base end 10a of the needle 10. Second end 12b of the filament is a free end distal from the first end 12a.

Suture filament 12 has a useful segment 13a and a terminal segment 13b. Terminal segment 13b is at the first end 12a of the filament 12. The useful segment 13a extends substantially from terminal segment 13b to the second end 12b of the filament 12. In applicant's experience, a remaining small length of suture filament 12 is retained attached to needle 10 once the last stitch is knotted during use of a particular suture. This is because the filament 12 becomes too short and thus stitches can no longer be easily tied with the remaining length of filament 12. This remaining length is referred to herein as the terminal segment 13b of filament 12.

The terminal segment 13b may be separated or detached, for example by cutting, from the useful segment along with the needle to be disposed of after the last formable suture knot is formed. As stated above, the terminal segment 13b is the left-over segment after a substantially last formable suture knot is formed using the useful segment 13a.

In one embodiment, in order to easily visually locate the terminal segment 13b after it has been severed from the useful segment 13a, the filament 12 is treated such that the terminal segment 13b has distinctive contrasting light frequency characteristics relative to the useful segment 13a.

In one embodiment, treatment of the terminal segment 13b includes impregnating the terminal segment 13b with a brightly colored dye and/or fluorescent dye. The fluorescent dye fluoresces a bright color when exposed to an ultraviolet (UV) light source. Therefore, a lost suture; that is, a suture that is disposed of and which contains the needle and the terminal segment, is located more easily because of the color contrast of the brightly colored terminal segment 13b against the dull color of standard drapes or flooring (including bodily fluids thereon) when the terminal segment 13b is exposed to UV light.

In order to enable easy location, it may not be necessary to impregnate the terminal segment 13b with a fluorescent dye. A brightly contrasting color in the terminal segment 13b may enable the terminal segment 13b to sufficiently standout so that use of UV light is not needed.

Distinctive contrasting light frequency characteristics may include, but not limited to, brightly coloring the terminal segment or treating or forming the terminal segment so that it is specularly responsive to an applied light source. An appropriate light source may include one or more of: UV sources, LEDs, lasers, incandescent lights or other light emitters as these would correspond to the desired light characteristic listed.

In another embodiment, in addition to the terminal segment having distinctive contrasting light frequency characteristics, the needle 10 may also have such distinctive contrast to enable ease of location of a lost suture.

In one embodiment of the invention, for color, needles 10 and/or the terminal segment 13b are colored with a bright pigment with high visibility and contrast. In another embodiment of the invention, for use with UV or so-called black light, needles 10 and/or the terminal segment 13b are impregnated with a fluorescent dye that imparts color when exposed to a UV light source. In another embodiment of the invention, needles 10 and/or the terminal segment 13b may be impregnated with material that has enhanced reflective properties to produce a characteristic glow or shine when exposed to a bright light so as to be specularly reflective.

Colorants or coloring agents referred to herein are preferably those that are approved for use by the US Food and Drug Administration.

It is advantageous that only the terminal segment 13b of the filament 12 is contrastingly adapted, so as to leave the useful segment 13a of filament 12 untreated. This is because small pieces or trimmed ends of filament 12 are, in applicant's experience, often dropped onto the drapes and floor as being merely a by-product of cutting the filament 12 after a knot is tied. These small pieces or trimmed ends advantageously should not light up under UV light or have contrasting visibility, as they are not attached to a needle and thus would distract from the search for a lost suture. It is thus desirable that such pieces or trimmings of filament remain in the background or ambient conditions as low-contrasting as they do not need to be located.

The terminal segment 13b of the suture filament 12 is not incorporated into the knots retained in the patient, and the treated terminal segment 13b of the filament and needle 10 thus only passes through patient tissue as the knotting is being done, without being left present in stitches remaining in the patient tissue thereby reducing the risk of irritation or inflammation of the tissue. In other words, the terminal segment 13b is adapted to pass through a tissue of a patient without leaving substantially any trace remaining in the tissue of a treated portion of the terminal segment 13b and/or needle 10.

In one embodiment of the invention, the suture filament 12 includes a terminal segment 13b configured to be in the range of one to three inches in length. In another embodiment of the invention, the suture filament 12 includes a terminal segment 13b configured to be preferably in the range of three to five inches in length. In another embodiment of the invention, the suture filament 12 includes a terminal segment 13b which is substantially ½ to ¾ inches long. Typically the larger the needle, the longer the suture filament.

In another embodiment of the invention, using smaller needles, the suture filament 12 includes a terminal segment 13b which is substantially one eighth of an inch to 2 inches long. Some sutures may be very small and the terminal segment 13b that is treated may only be ⅛ inch to ½ inch. Applicant believes that four inches is likely a convenient length limit with larger sutures in most instances. The length treated for each suture size would be adjusted to the anticipated length of the terminal segment and generally is 2-20% of the total length of the filament.

Thus, without intending to be limiting to exact dimensions or dimensionally based ranges: for size 0 or 2 sutures, a useful treated terminal segment length of the suture filament would be for example, two inches or so, or about five percent (5%) of a 36 inch long filament; or, for a 10/0 suture the terminal segment length would be for example 5-10 mm, or about four-to-eight percent (4-8%) of a five inch long filament. Thus, again without intending to be limiting, in one aspect of the invention a treated length of the terminal segment may be expressed as being within the ranges of for example 3-10% of the overall filament length, or for example in another embodiment in the range of 4-8% of the overall filament length, or by way of further example in an embodiment wherein the treated length of the terminal segment is substantially 5% of the overall filament length. As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

TABLE 1

Size of Sutures

| Old Gauge (USPD) | Diameter in mm |
|---|---|
| 8/0 | 0.05 |
| 7/0 | 0.07 |
| 6/0 | 0.1 |
| 5/0 | 0.15 |
| 4/0 | 0.2 |
| 3/0 | 0.3 |
| 2/0 | 0.35 |
| 0 | 0.4 |
| 1 | 0.5 |
| 2 | 0.6 |
| 3 | 0.7 |
| 4 | 0.8 |

Ref: Suture Material & Suturing technique - Dr. Anindya Chakrabarty

What is claimed is:

1. A method of using a suture comprising the steps of:
   (a) providing a suture which includes a needle and an attached filament, wherein the filament is attached to a base end of the needle, wherein the filament has a length consisting of a useful length and an adjoining remaining length, and wherein the remaining length is shorter than the useful length and wherein the remaining length forms a terminal segment of the filament and wherein the terminal segment is the end of the filament which is attached to the needle, and wherein the terminal segment of the filament is, or both the needle and the terminal segment of the filament are, distinctively contrasting in comparison to the useful length of the filament by means of contrasting light frequency characteristics and wherein said light frequency characteristics are chosen from the group comprising: fluorescently responsive to ultraviolet light, brightly coloured other than shades of red, differently coloured relative to the colour of blood, specularly responsive to an applied light source from a tool,
   (b) during surgery by a surgeon on a patient, wherein the surgery includes stitching using the useful length of the filament, forming at least one knot in the useful length of the filament during the stitching, (c) upon, during the stitching, running out of the useful length of the filament, then, after a last formable knot of the at least one knot is formed using the useful length of the filament, severing the terminal segment of the filament and needle from the useful length of the filament, (d) upon misplacement of the terminal segment of the filament and the needle once severed from the useful length of the filament, locating the misplaced terminal segment of the filament and the needle against a backdrop, including a bloody backdrop, of an open cavity in a patient receiving the stitching, a surgical gown of the surgeon doing the stitching, a surgical field associated with the surgery, surgical drapes associated with the surgery, or a surgical room floor associated with the surgery, by searching for and detecting the distinctive contrast of the terminal segment either visually or by using the tool to cause the distinctive contrast of the terminal segment.

2. The method of claim 1 wherein a length of said terminal segment is in the range of 4-8 percent of said length of said filament.

3. The method of claim 1 wherein a length of said terminal segment is substantially 5 percent of said length of said filament.

4. The method of claim 1 wherein said terminal segment has a treated portion which is treated to provide said contrast, and is adapted to pass through tissue of a patient without leaving substantially any trace remaining in the tissue of a treated portion of said terminal segment or needle.

5. The method of claim 1 wherein only said treated portion of said terminal segment is adapted to be fluorescently responsive.

6. The method of claim 1 wherein only said treated portion of said terminal segment is adapted to be brightly coloured.

7. The method of claim 1 wherein only said treated portion of said terminal segment is adapted to be differently coloured from the colour of blood so as to stand out when viewed against a red background.

8. The method of claim 1 wherein only said treated portion of said terminal segment is adapted to be specularly responsive to an applied light source.

9. The method of claim 1 wherein the tool is chosen from the group comprising: UV light emitter, black light emitter, LED, laser emitter.

10. The method of claim 9 wherein a length of said terminal segment is in the range of 3-10 percent of said length of said filament.

11. The method of claim 9 wherein the length of the terminal segment is substantially in the range of 2-20% of the total length of the suture filament.

* * * * *